United States Patent
Von Olleschik-Elbheim et al.

(10) Patent No.: US 10,393,664 B2
(45) Date of Patent: Aug. 27, 2019

(54) POINT-OF-CARE TEST SYSTEM AND METHOD FOR APPLYING A SAMPLE

(71) Applicant: DST DIAGNOSTISCHE SYSTEME & TECHNOLOGIEN GMBH, Schwerin (DE)

(72) Inventors: Lars Von Olleschik-Elbheim, Münster (DE); Mark Hunken, Schwerin (DE); Marc Dangers, Schwerin (DE)

(73) Assignee: DST DIAGNOSTISCHE SYSTEME & TECHNOLOGIEN GMBH, Schwerin (DE)

(*) Notice: Subject to any disclaimer, the term of this patent is extended or adjusted under 35 U.S.C. 154(b) by 352 days.

(21) Appl. No.: 15/191,573

(22) Filed: Jun. 24, 2016

(65) Prior Publication Data

US 2016/0305888 A1    Oct. 20, 2016

Related U.S. Application Data (63) Continuation of application No. 13/380,962, filed as application No. PCT/EP2010/059508 on Jul. 2, 2010, now Pat. No. 9,399,786.

(30) Foreign Application Priority Data

Jul. 2, 2009  (DE) ................ 10 2009 033 008

(51) Int. Cl.
| | |
|---|---|
| *G01N 33/53* | (2006.01) |
| *G01N 21/78* | (2006.01) |
| *B01L 3/00* | (2006.01) |
| *C12Q 1/00* | (2006.01) |
| *G01N 33/543* | (2006.01) |
| *G01N 33/558* | (2006.01) |

(52) U.S. Cl.
CPC ............. *G01N 21/78* (2013.01); *B01L 3/502* (2013.01); *B01L 3/5027* (2013.01); *B01L 3/50273* (2013.01); *B01L 3/502738* (2013.01); *C12Q 1/001* (2013.01); *G01N 33/54366* (2013.01); *G01N 33/54373* (2013.01); *B01L 2300/0681* (2013.01); *B01L 2300/0825* (2013.01); *B01L 2300/0864* (2013.01); *B01L 2300/0887* (2013.01); *B01L 2400/02* (2013.01); *B01L 2400/0406* (2013.01); *G01N 33/558* (2013.01)

(58) Field of Classification Search
None
See application file for complete search history.

(56) References Cited

U.S. PATENT DOCUMENTS 4,248,904 A    2/1981  Fenimore
5,366,902 A *  11/1994  Cox .................. B01L 3/502723
                                              422/402
(Continued)

FOREIGN PATENT DOCUMENTS

| EP | 0063810 A1 | 11/1982 |
| EP | 0119613 A2 | 9/1984 |
| EP | 0171150 A2 | 2/1986 |

(Continued)

*Primary Examiner* — Erik B Crawford (74) *Attorney, Agent, or Firm* — Drinker Biddle & Reath LLP (57) ABSTRACT

The present invention relates to a test system or assay system (detection system) and to a test method, preferably in use in the point-of-care (PoC) field.

15 Claims, 3 Drawing Sheets

(56) References Cited

U.S. PATENT DOCUMENTS

| | | |
|---|---|---|
| 6,696,240 B1 | 2/2004 | Kloepfer et al. |
| 2004/0053352 A1 | 3/2004 | Ouyang et al. |

FOREIGN PATENT DOCUMENTS

| | | |
|---|---|---|
| EP | 0791829 A2 | 8/1997 |
| WO | WO-84/01031 A1 | 3/1984 |
| WO | WO-92/07655 A1 | 5/1992 |
| WO | WO-02/72264 A1 | 9/2002 |
| WO | WO 2007/060580 A1 | 5/2007 |

* cited by examiner

POINT-OF-CARE TEST SYSTEM AND METHOD FOR APPLYING A SAMPLE

CROSS-REFERENCE TO RELATED APPLICATION

This application is a continuation application of Ser. No. 13/380,962, filed Apr. 23, 2012 which is based on the National Stage of PCT/EP2010/059508, filed Jul. 2, 2010, both of which are incorporated by reference herein in their entirety. This application also claims the benefit of German Application No. 10 2009 033 008.9, filed Jul. 2, 2009 and incorporated by reference herein in its entirety.

BACKGROUND OF INVENTION

The present invention relates to a test system or assay system and a test method, preferably for use in a point-of-care (PoC) testing field.

For purposes of research, diagnostics and a plurality of other applications, analytical laboratory tests which are used for qualitatively and/or quantitatively analyzing molecules, analytes or the activity or composition thereof, form the basis for far-reaching conclusions, including the development of new methods or apparatus. Said tests are based upon the generally known methods of DNA/RNA analysis and/or protein analysis. Another example involves the multitude of analytical processes and methods that are used for antibody reactions, so-called immune reactions, which are used for analyzing (bio)markers and many other substances/analytes.

Rapid test methods are known, such as the lateral-flow test (LFT), the flow-through test (FTT), the agglutination test (AT), and the solid-phase test (SPT). All of these methods are used for rapidly testing for analytes without the use of equipment, and are suitable for visual analysis.

One sound assay principle that is known is described in the prior art of in-vitro diagnostics as an immunoassay (IA), particularly as EIA, or a "binding assay" ("sandwich") (see, e.g., EP0171150 B1, EP 0063810B1). A fluorometric assay for IgE within the framework of a binding assay is also known from EP 0119613 B1, for example.

Reference is also made to the publications of Roger P. Ekins (e.g., WO 8401031, etc.).

Additionally, a membrane-based binding assay, particularly of IgE from blood to allergens, has been known since the end of the 1980's. For example, CHEMICAL ABSTRACTS, Vol. 101, No. 25, 17 Dec. 1984, page 578, abstract no. 228190b, Columbus, Ohio, US; B. J. WALSH, et al.: "Allergen discs prepared from nitrocellulose: detection of IgE binding 1-:o soluble and insoluble allergens", & J. IMMUNOL. METHODS 1984, 73(1), 139-45.

For the field of PoC testing, the commercially available fast-check PoC of the applicant is described, for example (see EP1718970), which can be used on the basis of a membrane-based binding assay for assaying allergens from whole blood.

However, there is a significant need for improvement of an assay system for a PoC testing system.

One particular problem is that of ensuring the coincident or simultaneous sample wetting of the individual test sites. This is essential for ensuring reproducibility and for achieving a high-quality result.

A similarly serious problem is that of ensuring that the test sites are wetted with the same quantity of sample fluid in each case.

Tube systems, such as are described in WO2002072264 for immunoassays, for example, and are designed to allow a controlled and selective supply of sample to a membrane, are known in the prior art.

However, it is a drawback that the known channel or tube systems do not ensure a uniform application or homogeneity of the individual samples from an overall sample pool.

The invention therefore addresses the problem of providing an improved sample infeed for a PoC test system, which produces a better result.

This problem is solved in a surprising manner by claim 1. According to the invention, a test method is provided, wherein
 a. At least one test reagent is fixed on a first surface, and a second surface is formed on the back side thereof,
 b. At least one sample fluid is conducted in a sample channel, wherein the sample channel leads to a discharge area, which is disposed opposite the second surface, wherein the second surface is wettable at least in one region that is opposite the discharge area,
 c. And the sample fluid exits the sample channel through the discharge opening thereof as a result of applied pressure, and said fluid forms a drop that adheres to the discharge area opening,
 d. Wherein contact is produced between the drop and a wetting point on the second surface, in that, as a result of the pressure applied to the sample channel, the drop is enlarged such that the drop comes into contact with the wetting point,
 e. The sample fluid, as a direct result of the stated contact with the wetting point, or as a result of the capillary action of the first surface and/or the pressure applied to the sample channel, penetrates from the second surface toward the first surface or travels up to the first surface and reacts with the test reagent.

Additional advantageous methods of implementation and embodiments result from the dependent claims.

A test reagent can contain substances, for example, such as peptides, proteins, enzymes or substrates thereof, ligands or receptors, antibodies or antigens, DNA, RNA, PNA, but also molecules of a non-biochemical origin, such as iodine, for example. The test reagents can contain combinations of these types of molecules or fragments thereof, or conjugates, in modified forms, for example, glycolized or phosphorylated. Lipids and sugars are also covered by the invention. Natural substances and natural extracts can also be present in test reagents, as is frequently the case with allergy tests or nutritional intolerance tests.

The discharge area and/or the first and/or the second surface of a test carrier can be made, for example, of glass or plastic, particularly transparent plastic. Polycarbonates such as macrolon, polycyclic olefins such as topaz, polypropylene, PMMA or polyimides are preferred. The area can also be coated, for example, with proteins, more particularly, antibodies, sugars such as dextrans, or with metals, glass or plastics, or with carbon derivatives such as carbon nanotubes, for example.

One or more test reagents are fixed on the first surface. According to the invention, the test reagents can be fixed in a layer underneath the first surface. For example, the test reagents can be dried onto the surface, either alone or in a stabilizing matrix, or can be applied as a lyophilisate and can be released from the surface during wetting. The test reagents can further be fixed by way of non-covalent interactions, such as occur between antibodies and protein A, between biotin and streptavidin, between hexahistidine and nickel-NTA or with the base pairs of DNA, for example. An element of the test reagents can also be bonded covalently to the first surface. In a preferred embodiment, the test reagent remains essentially fixed to the first surface during wetting, particularly by more than 50%.

A sample fluid can be any substance or mixture of substances, optionally including solvents, of any origin, particularly from a vegetable or an animal, more particularly from a mammal, more particularly from a human. The sample fluid may be, but is not limited to, whole blood, half blood, serum, saliva, tears, urine, secretions, cranial fluid or processed forms of such fluids, such as EDTA—stabilized blood, for example.

The sample channel can comprise a means for applying pressure. In a preferred embodiment, said means can be a fill opening or a fill port, into which a syringe is inserted, for example, with which a user can apply pressure manually. Other embodiments comprise blisters or pump chambers, or connections for external pumps. A heating device can also be provided, with which the fluid is expanded or brought to evaporation, thereby building up pressure.

The discharge area can be designed to be wettable in the region of the discharge opening of the sample channel, so that the drop that forms when pressure is applied will adhere and will not detach in an uncontrolled fashion. This property according to the invention can be provided, for example, by polycarbonates such as macrolon and polyolefins such as topaz, in untreated form, or post-treated, as long as the post-treatment, such as plasma treatment, does not decrease or only slightly decreases wettability. This wettable region can be surrounded by a hydrophobic region, with which the drop size can be limited.

The second surface is designed to be wettable in the region of the wetting point that is disposed opposite the discharge opening, so that the drop comes into contact with the second surface. More particularly, this region can be made of nitrocellulose.

In the method, it is particularly preferable for the second surface at the discharge opening of the sample channel to be spaced from the discharge area by 0.001 mm to 15 mm, especially by 0.01 mm to 2 mm, more particularly by 0.04 to 0.4 mm.

The wetting point lies on the second surface and is the first point on this surface that comes into contact with the drop as it grows on the second surface. Particularly preferable are embodiments in which the wetting point is fully reproducible, in that it can be produced by the stated hydrophobing of the discharge area and/or by hydrophobing around the wetting point on the second surface and/or particularly preferably by a widened area around the terminal opening of the sample channel.

In a particularly preferred embodiment of the method, the sample channel is therefore embodied such that it is widened at its end that faces the second surface, so that the drop at least partially or fully wets the surface of the widened area. According to the invention, the widened area extends from the discharge opening of the sample channel up to the discharge opening edge of the widened area.

According to the invention, the widened area is wettable in the region of the discharge opening edge. It can be preferable for the region of the discharge opening edge of the widened area to be made hydrophobic.

Advantageously, as a result of the widened area, the contact angle and the surface of the drop are optimal in terms of energy when the drop forms in the widened area. For expansion beyond the boundaries of the widened area, however, more energy must be applied. Therefore, the widened area causes the drop to assume an advantageously stable and reproducible position and shape. The wetting point on the second surface and the point of passage of the sample fluid on the first surface are thereby advantageously precisely determined.

In the method, it is particularly preferable for the discharge area at the position on the discharge opening edge of the widened area to be spaced from the second surface by 0.001 mm to 15 mm, especially by 0.01 mm to 2 mm, more particularly by 0.04 to 0.4 mm.

In a further embodiment, the second surface can end or can lie at least partially on at least one discharge opening edge of a widened area, or an intermediate space is formed from the second surface up to the discharge opening edge of the widened area. The space that is formed represents a cavity, which can be delimited spatially (e.g., by means of a housing, side walls, etc.).

In addition, the individual discharge opening edges of the widened area are preferably formed in a single discharge area, which lies opposite the first and second surface and/or rests entirely or partially on the second surface.

An intermediate space can therefore take on different volume columns from the second surface or the first surface for one of each of the discharge opening edges of a widened area. For example, the plane of the second surface can be inclined relative to the discharge area of all the sample channels/widened areas. More particularly, the second surface can rest partially on the planes of the discharge opening edges of the widened areas, either at the discharge opening edges of the widened areas or next to the widened areas.

In the method, it is particularly preferable for the widened area on the discharge side of at least one of the sample channels to be embodied as conical or concave, more particularly, semispherical, in the shape of a plate or a spherical segment. The widened area can also have any approximately oval or essentially concave shape. The widened area can also have a cylindrical shape, or can generally have edges and kinks. It can be preferable for the widened area to be trumpet-shaped.

In a preferred embodiment, the widened area at the discharge opening edge has a diameter of between 0.015 and 15 mm, especially between 0.1 and 6 mm, more particularly, between 1 and 4 mm.

In a preferred embodiment, the widened area has a depth, i.e., a distance from the discharge of the sample channel up to the discharge opening edge of the widened area of 0.001 mm to 2 mm, more particularly, between 0.01 and 1 mm.

The sample channel can also have a discharge port, as long as said port does not restrict the wetting of the widened area.

The widened area can deviate from a radially symmetrical shape, for example, it can be elliptical or oval, or can have an irregular cross-section.

Also preferable is a nearly equal distance between the second surface and the discharge opening edges across a large portion of the first surface and across a plurality of wetting points. It is further preferable for the first and/or second surfaces to extend parallel and/or planar to the planes of the discharge opening edges or discharge opening areas of all sample channels/widened areas.

It is possible, on the basis of manufacturing techniques, that this distance between discharge area and second surface cannot be precisely maintained or is not stable, for example, if a membrane is used as the first surface and the second surface. The method according to the invention has the particular advantage that even under this circumstance, the wetting points can still be wetted nearly uniformly and simultaneously.

Particularly preferable is an embodiment in which at least one (test or assay) reagent, more particularly, a washing solution and/or a stop solution, is supplied for the test.

One or more channels can lead from various directions to the site in which a test reagent is fixed, and/or to the wetting point. It is preferable for the additional channel to be arranged perpendicular to the line comprising sample channel—wetting point (second surface)—optionally passage point (first surface). More particularly, the additional channel can supply a plurality of assay sites in series or in parallel with a reagent. The reagent can be a stop reagent, for example, which stops an enzymatic reaction, for example, in the case of an ELISA. The reagent can contain a substrate, for example, which initiates light emission in a luminescence method (Firefly). Particularly preferred is an embodiment in which a marked secondary antibody is supplied. It is further preferable to supply a washing solution, for example, in order to wash non-binding antibodies away from the assay site. It can be preferable to supply a plurality of (test) reagents in series through the same channel.

Also preferred is an embodiment in which the discharge area and the second surface are rigidly connected to one another, in which particularly the volume between the discharge of the sample channel, including the widened area, and the second surface, optionally including the intermediate space, is closed off in relation to the surrounding area and forms a first cavity, and in which the air within this volume is able to escape through an additional channel or through at least one additional opening. The first cavity can have different shapes, as long as it ensures that the drop can come into contact with the first surface. Particularly preferable is an embodiment in which the cavity of at least one discharge opening of a sample channel has a distance from the discharge opening to the second surface of 0.001 mm to 15 mm, especially 0.01 mm to 2 mm, more particularly 0.04 to 0.4 mm.

This cavity can further encompass an intermediate space as described above.

Particularly preferable is an embodiment in which the first and/or second surface consists of a gel-type, porous, screen-like, permeable or semi-permeable membrane, or a dialysis membrane, particularly a coated or uncoated nitrocellulose membrane.

According to the invention, the first and/or second surface can be fully or partially connected to the substrate material of the cavity. It can also be applied as a coating and can be produced in situ by known microengineering methods, for example, by imprinting, vapor deposition or sol-gel methods, and can be detached from its substrate by dissolving a previously applied sacrifice layer. The first and/or second surface can be structured by known methods, for example, by applying a protective mask to regions that are to be retained, followed by etching or plasma processing. The first and/or second surface can be composed of a plurality of layers and can be processed in situ, for example, holes can be produced in the first and/or second surface using a laser, or at least one of the layers thereof can be functionalized by plasma processing or using biomolecules.

It can be preferable for the distance between the first and the second surface to range from 0.001 to 1 mm. In one preferred embodiment it is monomolecular.

In one preferred embodiment, a membrane is produced at least partially by an outside source, and after these production steps is applied to a surface or positioned between such surfaces. For example, the membrane can be glued to at least a part of the area of said surface, fixed by a static charge, or mechanically clamped, particularly between the first and the second surface, or can be fastened by a combination of different methods.

According to the invention, the membrane is provided outside with at least one test reagent prior to being positioned. Test reagents can be applied to the membrane using a dispensing unit, by discharge from an object, particularly a tube with or without a backfill device, by an imprinting process, for example, screen printing, by photochemical fixation or by means of a spray. Linker molecules can also be anchored to the membrane, to which molecules the molecules of the test reagent then bond, without significantly influencing the bonding of the analytes from the sample fluid.

In another embodiment, at least some of the test reagent is applied in situ. In this case, the methods listed above may be used, for example.

In a particularly preferred embodiment, the membrane is absorbent to water, so that the sample fluid will expand further onto or into the membrane after the wetting site has been wet with the drop. Expansion can occur by capillary action and/or by continuous pressure applied by the sample fluid. More particularly, the membrane can consist of a non-woven material, more particularly nitrocellulose.

It can be preferable to attach the membrane to an additional material, for example, cotton wadding, which increases the capacity for capillary action, i.e., absorbency.

It is particularly preferable to position the membrane in the cavity in the form of at least one strip, more particularly, in a parallel positioning.

In a particularly preferred embodiment, the membranes or strips are spotted or imprinted with test reagents, or the test reagents are applied by contact.

In a particularly preferred embodiment, the test reagents are applied in the form of strips, squares or rectangles, circles, numbers or letters, or symbols. It is particularly preferable to apply other black/white, grey, or colored symbols in advance without a test reagent, so that, for example, a "−" symbol applied in advance can be changed to a "+" symbol.

In a particularly preferred embodiment, the test reagent is applied as a strip to the membrane, and extends from one edge of the membrane to the other. Particularly preferably, the membrane is strip-shaped, and the strips of test reagent extend from one longitudinal edge of the membrane strip to the opposite longitudinal edge.

In one preferred embodiment, a second cavity is located on the first surface, which cavity is independent of the cavity formed on the second surface, with at least one microfluid channel discharging into said second cavity and connecting said second cavity to a reservoir or to the surrounding area.

The second cavity can be different in shape without thereby adversely affecting the method according to the invention. More particularly, it can be preferable for microfluid channels, which are connected to a reservoir or to the surrounding outer area, to discharge into the second cavity.

In a preferred advantageous embodiment, no test reagent is located at the point of passage on the first surface. According to the invention, a passage point of this type on the first surface lies opposite the first wetting point on the second surface. As soon as the drop comes into contact with the wetting point of the second surface, the sample fluid spreads by way of capillary action and/or pressure onto the membrane, reaching at least one assay site with test reagent, which can lie on a stated, covered partial region of the membrane. In this embodiment, the membrane on the first surface not only carries the test reagent, but also prevents larger particulate constituents of the sample fluid from coming into contact with the test reagent.

This embodiment advantageously prevents larger constituents in a sample fluid, such as erythrocytes in a whole blood sample, for example, from interacting with the test fields.

Therefore, the invention also relates to embodiments in which the point of passage on the first surface is free of test reagents.

In a further embodiment, at least two, more particularly, at least ten assay sites are positioned at separate locations on the first surface. Some of the sites can also be provided for control tests.

Preferably, various assays, particularly for various allergens or nutritional intolerance substances, can be carried out on different assay sites.

In a preferred embodiment, at least two sample channels, each having a widened area, open up into the discharge area, and at least two of these sample channels are connected via at least one branch to at least one shared reservoir or one shared fill opening.

In a particularly preferred embodiment, at least one sample channel has a narrowed area or flow restrictor that increases flow resistance near its end, upstream of the widened area, said restriction being achieved according to Hagen-Poiseuille by reducing and/or modifying the shape of the cross-sectional area of the sample channel. The cross-sectional area is preferably reduced by more than 1%, especially by more than 10%, more particularly, by more than 30%. Particularly preferable is a modification of an angular cross-section of 0.5*1 mm to a round diameter of 0.5 mm. The cross-section of the restrictor can deviate from that of the sample channel, and can have square, round or irregular cross-sections. It can be preferable to vary the cross-section in terms of shape or size over the length of the restrictor. In a further embodiment, the restrictor does not extend straight, and instead has a bent or meandering profile.

In a further preferred embodiment, the length of the narrowed area of the respective sample channel is 1 cm to 0.5 mm.

In a preferred embodiment, the narrowing is implemented in the form of a step.

It can be preferable for the sample channel to deviate perpendicular from the first sample channel, or at an angle of 40 to 120 degrees in relation to the longitudinal axis of the first sample channel.

In a preferred embodiment, one or more sample channels originate from a first sample channel, wherein the transition from the first sample channel to the at least one subsequent sample channel comprises a reduction in cross-section, which also serves as a restrictor.

In a particularly preferred embodiment, one or more sample channels, especially four, in intersecting form originate from a first sample channel.

In a preferred embodiment, at least two discharge openings, particularly all discharge openings, of the sample channels originate from a common fill port.

In a preferred embodiment, the cross-sections of the sample channels are different, and are configured such that the different flow resistances of the sample channels are equalized. As a result, the different samples flow at the same time and in the same amounts into the widened area, even if the lengths of the channels or the number of the angles or curves per sample channel are different. Consequently, the sizes of the drops that form in different widened areas are approximately equal in this embodiment.

In a further embodiment, the narrowing according to the invention can be produced in the form of a screen-like structure, which is positioned essentially transversely to the longitudinal axis of the sample channel. The diameter of the individual screen openings can be different, and their arrangement irregular. Particularly preferable is a square or hexagonal arrangement of the screen openings. In a further preferred embodiment, the screen openings become larger toward the edges, in order to level out the laminar flow profile in the sample channel.

It can further be provided, with two or more sample channels, to vary the diameter of the narrowed areas such that different sample channels have the same flow resistance irrespective of the different lengths thereof.

This narrowing or reduction in diameter along the respective sample channel permits an optimal homogeneous distribution of the individual samples from an overall sample pool, since a restriction of flow along the flow gradient is achieved, and in this manner, a simultaneous drop formation at the outlet of the sample channel leads to optimal wetting on the membrane. If the sample channels are filled with sample fluid through a shared fill opening, first the sample channels fill simultaneously. When a narrowed area is reached, the sample fluid first stops, and the other sample channels continue to fill, until the narrowed area is reached in all channels. Only then does the sample fluid penetrate through the narrow points into the widened areas, at each of which a drop is formed.

In this case, wetting by means of a plate that is open radially toward the top is particularly appropriate, because a plate of this type supports the formation of a drop. The drop serves to overcome the distance between the sample channel and the membrane, and is dependent upon the diameter of the outlet discharge from the channel. In other words, the plate shape causes a substantial enlargement of the drop shape, and causes the sample to be brought into contact with the membrane material at the wetting site. The membrane then assumes an absorbent role, in which, after contact is established with the sample, the membrane absorbs sample passively until the membrane is saturated.

In a further embodiment, the flow of each sample channel can be restricted independently of the other channels. A restriction of this nature can be implemented, for example, by way of a valve, or simply by way of a reservoir, wherein a first sample channel has an angle measuring 40-120 degrees.

In a further preferred embodiment, at least two test reagents are arranged in such a way that they are positioned on the first surface or the membrane radially around a wetting point, at equal or different distances or angles, so that in a straight line of connection between a fixed test reagent and the wetting point, no additional fixed test reagent is located. This configuration prevents the sample fluid from running across different assay sites and prevents the data of these assay sites from influencing each other, for example, by antibodies from the samples cross-reacting.

In a preferred embodiment, a plurality of membranes, particularly strip-shaped membranes, are arranged in parallel, and the second cavity consists of one or more parallel partial cavities. More particularly, a second cavity can be dimensioned such that it extends across a plurality of assay sites, preferably all assay sites, of a membrane strip. It is also preferable for the second cavity to extend a similar distance across a membrane strip. It is further preferable for the membrane strip to separate first and second cavity completely from one another, and to prevent any sample fluid from passing from the first cavity into the second cavity, without passing through the membrane.

In a particularly preferred embodiment, the second cavity is connected to a fill port, through which test reagents or washing solutions can be filled into the second cavity by means of a syringe, a water column, a pump or some other device for generating pressure. In a particularly preferred embodiment, this cavity is connected to an outlet opening or to a waste receptacle, so that air and excess fluid can escape from the second cavity. Preferably, in addition to the second cavity, additional cavities or partial cavities having shared fill ports or waste receptacles are connected to one another.

In a preferred embodiment, at least one lens is positioned above at least one fixed test reagent, so that even small assay sites can be easily identified by the human eye.

In a preferred embodiment, the test reagent is lyophilized and/or is coupled covalently or non-covalently to the first surface or membrane.

In a preferred embodiment, the pore size of the first surface or membrane is such that proteins are able to pass through the pores, but erythrocytes and white blood corpuscles are not. More particularly, a pore size of less than 0.8 µm is preferred, most particularly of less than 0.2 µm.

In a preferred embodiment, the test method comprises a binding assay. In this case, binding between peptides and/or proteins or DNA-, RNA- or PNA hybridization, antibody/antigen binding, aptamer-target binding, primary/secondary antibody interaction, ligand/receptor interaction or combinations thereof can be used, for example. Particularly preferable is a binding assay in which an antigen is fixed to the first surface, the sample fluid contains antigen-specific IgE, and an anti-IgE antibody is added, which carries an enzymatic, fluorescent, luminescent or colored marking.

The invention further relates to a test system consisting of a first surface and a second surface, wherein
   a. at least one test reagent is fixed onto a first surface, and a second surface is formed on the reverse side thereof,
   b. wherein the sample channel leads to a discharge area, which is disposed opposite the second surface, wherein the second surface is wettable at least in one area that is opposite the discharge area,
   c. wherein the sample channel is widened at its end that faces the second surface,
   wherein the discharge opening edge of the widened area is spaced from the second surface by 0.001 mm to 15 mm, especially by 0.01 mm to 2 mm, more particularly by 0.04 to 0.4 mm, and the first surface and the second surface each foam a cavity, independently of one another.

The test system can be configured appropriately using the above-mentioned features, even if said features refer to the method according to the invention. Additional details are specified in the claims and in the figures.

EXAMPLES AND FIGURES

These examples serve exclusively to illustrate the invention, and are not intended as a restriction of the invention thereto.

Example 1

A) 100 µl peripheral blood, or serum, or whole blood to which heparin is added is drawn.
B) The sample is mixed with the assay solution
C) The solution is placed in the test housing, with the assay fields being homogeneously moistened starting from the first surface
D) 5 minutes of incubation time
E) The reverse side of the first surface, which carries the test, is washed 3× with 1 ml washing fluid each, with incubation time between the 1 ml washing steps
F) The substrate is input via the reverse side of the membrane, 5 minutes of incubation time
G) The reaction is stopped by adding stop solution via the reverse side of the membrane
H) The assay fields are analyzed visually

DESCRIPTION OF THE FIGURES

FIG. 2 illustrates the wetting process according to the invention. The block arrows at the bottom of the drawing indicate the direction of expansion of pressure in the fluid. (Left) The sample fluid exits the restrictor and forms a drop in the widened area. (Center) The drop grows and comes into contact with the membrane at wetting point (10). (Right) The sample fluid spreads in the membrane, in the direction (11) of the assay sites.

Figure 1A:
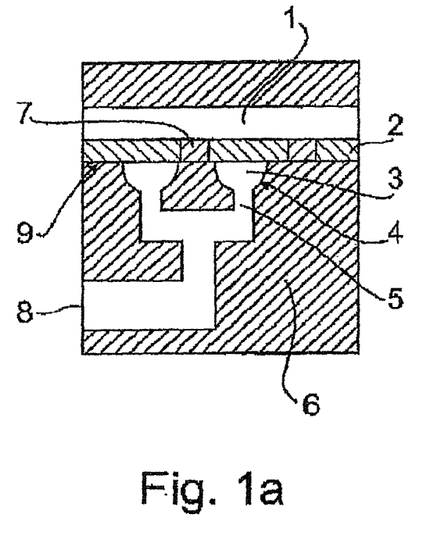
FIG. 1(a) shows a possible configuration consisting of a second cavity (1), a membrane (2), a widened area (3), a surface (4) of the widened area (3), a narrowed area or restrictor (5), a substrate (6), an assay site (7) with test reagent and a sample channel (8) and discharge area (9).
Figure 1B:
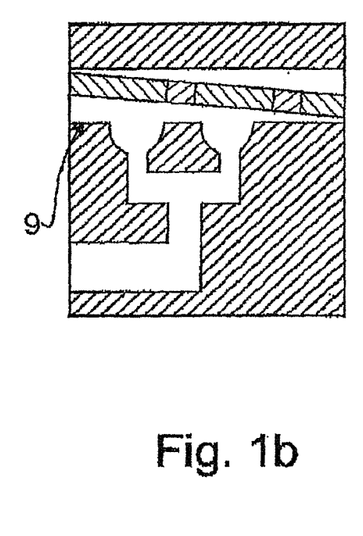
FIG. 1(b) shows that when the membrane does not lie on the discharge area (9) or is inclined at an angle, the arrangement ensures a nearly uniform wetting (inclined position of the membrane in the drawing is exaggerated for purposes of clarity).
Figure 2:
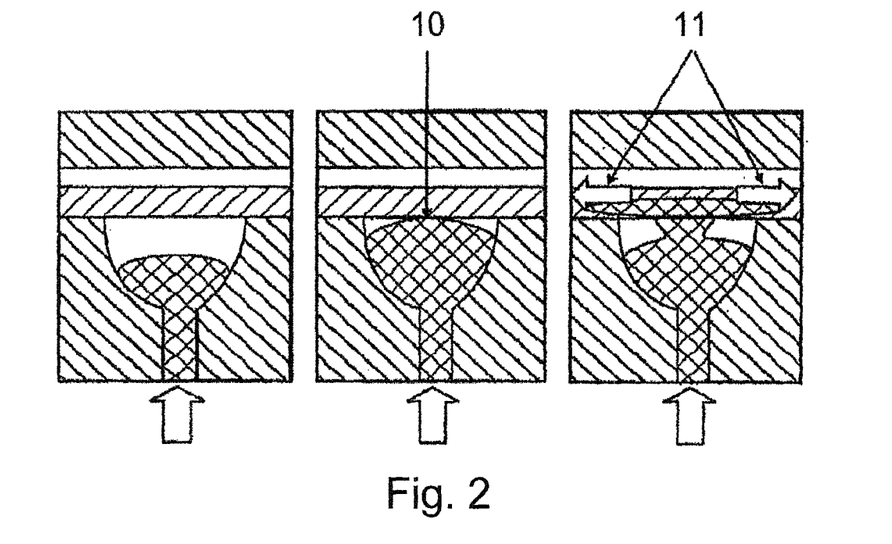
Figure 3:
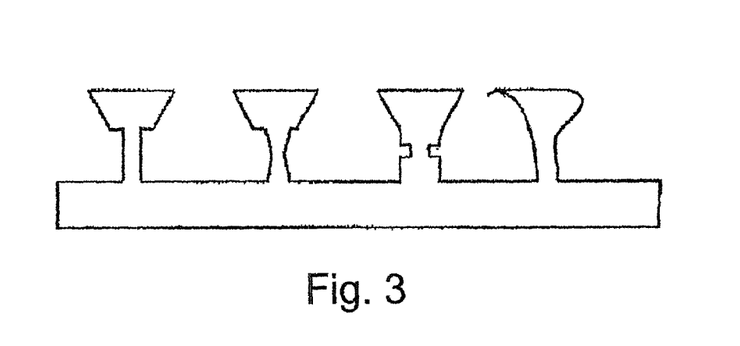
FIG. 3 shows different forms of the narrowed area or restrictor, in a longitudinal cross-section. The widened areas are each illustrated as trapezoids. The form on the far right side is a trumpet-shaped widened area.
Figure 4A:
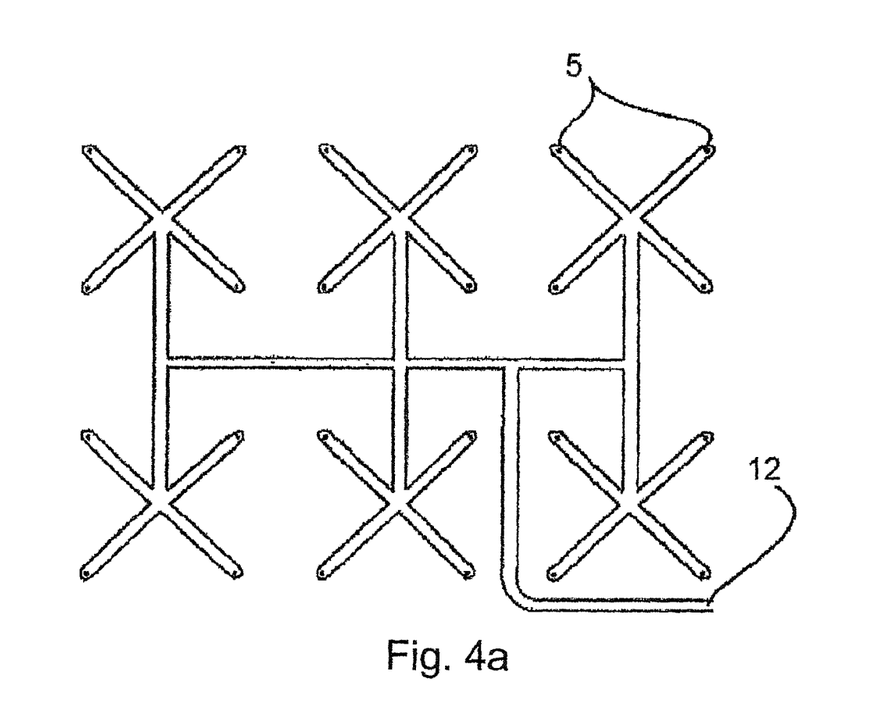
FIG. 4(a) illustrates the distribution of the sample fluid in the sample channels, which fluid is conducted from a shared fill port (12) via cross connectors to the restrictor (5) and to the connected widened areas.
Figure 4B:
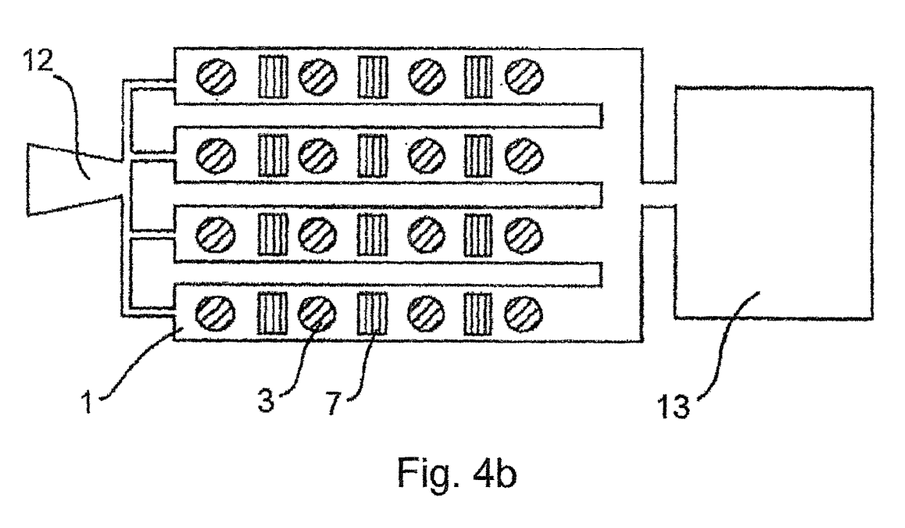
FIG. 4(b) schematically illustrates the plane of infeed of the washing solution via the shared fill port (12); with the second cavities (1), in which the membranes lie; the indicated widened areas (3) on the underside of the membrane (second surface), along with the assay sites (7) to a waste receptacle (13).

The invention claimed is:

1. A test method comprising:
   a) applying a sample fluid in a sample channel of a test system, wherein the sample channel leads to a discharge area and a membrane, wherein the membrane comprises a first surface having at least one test reagent fixed thereon and a second surface formed on the reverse side of the first surface, wherein the second surface is facing the discharge area and has a wetting point, wherein the sample channel comprises a narrowed area connected to a widened area at its end that faces the second surface through a discharge opening, and wherein the widened area ends in the discharge area with a discharge opening edge;
   b) applying pressure to the sample channel so that the sample fluid passes through the discharge opening from the narrowed area and forms a drop that adheres to the discharge opening;
   c) enlarging the drop by applying pressure to the sample channel until the drop contacts the wetting point on the second surface; and d) allowing the sample fluid to penetrate from the second surface toward the first surface to react with the at least one test reagent.

2. The test method of claim 1, wherein the edge of the discharge opening is hydrophobic.

3. The test method of claim 1, wherein the drop at least partially wets the widened area.

4. The test method of claim 1, wherein the discharge opening edge is spaced from the second surface by 0.001 mm to 15 mm.

5. The test method of claim 1, wherein the discharge opening edge has a diameter of between 0.015 and 15 mm.

6. The test method of claim 1, wherein the widened area has a depth of 0.001 mm to 2 mm.

7. The test method of claim 1, wherein the second surface ends on the discharge opening edge of the widened area or lies at least partially on the widened area or beside the widened area.

8. The test method of claim 1, wherein the widened area is conical or concave in the form of a plate or a spherical segment.

9. The test method of claim 1, wherein at least one additional reagent is supplied to the sample channel.

10. The test method of claim 1, wherein the first surface and/or the second surface consists of a porous, permeable, semipermeable, or dialysis membrane.

11. The test method of claim 1, wherein a point of passage is located on the first surface and is free of the at least one test reagent.

12. The test method of claim 1, wherein the first surface and the second surface each forms a cavity independently of one another.

13. The test method of claim 1, wherein the narrowed area has a reduction in cross-sectional area of more than 1%.

14. The test method of claim 1, wherein the sample fluid reacts with the at least one test reagent in a binding assay.

15. The test method of claim 1, wherein the sample fluid is whole blood, serum, saliva, tears, urine, secretions, or cranial fluid.

* * * * *